United States Patent [19]
Wong

[11] Patent Number: 4,786,500
[45] Date of Patent: Nov. 22, 1988

[54] PROGRAMMABLE AGENT DELIVERY SYSTEM
[75] Inventor: Patrick S.-L. Wong, Hayward, Calif.
[73] Assignee: ALZA Corporation, Palo Alto, Calif.
[21] Appl. No.: 878,947
[22] Filed: Jun. 26, 1986
[51] Int. Cl.[4] .................. A61K 31/74; A01N 25/26; A61J 3/00
[52] U.S. Cl. .................................. 424/422; 424/424; 424/427; 424/430; 424/468; 424/472
[58] Field of Search ................ 424/21, 427, 436, 430, 424/472, 422, 424, 468

[56] References Cited
U.S. PATENT DOCUMENTS

| | | | |
|---|---|---|---|
| 4,008,719 | 2/1977 | Theeuwes et al. | 604/893 |
| 4,014,334 | 3/1977 | Theeuwes | 604/893 |
| 4,058,122 | 11/1977 | Theeuwes | 604/893 |
| 4,077,407 | 3/1978 | Theeuwes et al. | 424/427 |
| 4,111,203 | 9/1978 | Theeuwes | 604/892 |
| 4,160,020 | 7/1979 | Ayer et al. | 424/427 |
| 4,160,452 | 7/1979 | Theeuwes | 424/427 |
| 4,256,108 | 3/1981 | Theeuwes | 604/893 |
| 4,432,964 | 2/1984 | Shell et al. | 424/427 |

Primary Examiner—Joseph L. Schofer
Assistant Examiner—Peter F. Kulkosky
Attorney, Agent, or Firm—Paul L. Sabatine; Edward L. Mandell; Steven F. Stone

[57] ABSTRACT

This invention pertains to a programmable delivery system.

1 Claim, 2 Drawing Sheets

PROGRAMMABLE AGENT DELIVERY SYSTEM

FIELD OF THE INVENTION

This invention pertains to a novel and unique programmable useful agent delivery system. The delivery system can be programmed to deliver useful agents at time-varying patterns of delivery comprising agent-free intervals between agent-pulses of various duration.

BACKGROUND OF THE INVENTION

Presently, in the fields of pharmacy and medicine, prolonged or sustained medicators have as their primary goal the delivery of a beneficial agent at a constant rate over an extended period of time. However, many therapeutic programs require the dose of medication administered to a warm-blooded animal comprise rate-programmed intervals for extended time periods. For example, the Ferring Zyklomat pump was designed to deliver gonadotropin-releasing hormone (GnRH) in a pulsatile regimen as the physiological pattern in primates as disclosed in a paper presented at the *Robert First Conference*, Oct. 7 and 8, 1985, Philadelphia, PA. The therapeutic value of drug rate-programmed intervals was reported for bleomycin free-intervals in cancer therapy in *Cancer Treat. Rep.* Vol. 62, pp. 2011 to 2017, 1980. The pharmacokinetics of interval doses by intravenous infusion of gentamicin in subtotal nephrectomized dogs was reported in *Toxicol. Appl. Pharmacol.* Vol. 75, pp. 496 to 509, 1984. Also, in antibiotic therapy, and in desensitizing against allergens, it is desirable to provide a therapeutic program consisting of a single dose of the drug followed by a delayed dose of drug for optimum therapy. Thus, it is evident from the above presentation a need exists for programmable delivery system that can provide the desired time profile of drug administration to achieve the intended and beneficial effect.

OBJECTS OF THE INVENTION

Accordingly, it is a primary object of this invention to provide a programmable agent delivery system that represents an unexpected improvement in the dispensing art and substantially fulfills the pressing need of the prior art.

Another object of the present invention is to provide a programmable agent delivery system adapted as a dosage form for rate-programmed drug delivery at time-varying patterns.

Another object of the present invention is to provide a dosage form comprising means for providing drug-free intervals between drug pulses of various durations.

Another object of the present invention is to provide a dosage form that can deliver a pulsed dose of a beneficial drug, then delay the delivery of the drug, and then deliver a pulsed dose of drug.

Another object of the present invention is to provide a dosage form comprising at least two timed spaced-apart doses of drug in a single dosage form.

Another object of the invention is to provide a dosage form comprising two doses of drug in a single dosage form that can be used for twice a day dosing of the drug.

Another object of the present invention is to provide a novel dosage form manufactured in the form of a drug delivery device comprising means for delivering a pulsed dose of drug, means for providing a drug-free interval, and means for then providing a recurring pulsed dose. Other objects, features and advantages of the invention will be more apparent to those versed in the dispensing art from the following specification, taken in conjunction with the drawing figures and this accompanying claims.

BRIEF DESCRIPTION OF THE DRAWING FIGURES

In the drawing figures, which are not drawn to scale, but are set forth to illustrate various embodiments of the invention, the drawing figures are as follows.

In the drawing figures and in the specification, like parts in related figures are identified by like numbers. The terms appearing earlier in the specification, and in the description of the drawing figures, as well as embodiments thereof, are further described elsewhere in this disclosure.

DETAILED DESCRIPTION OF THE DRAWING FIGURES

Figure 1A:
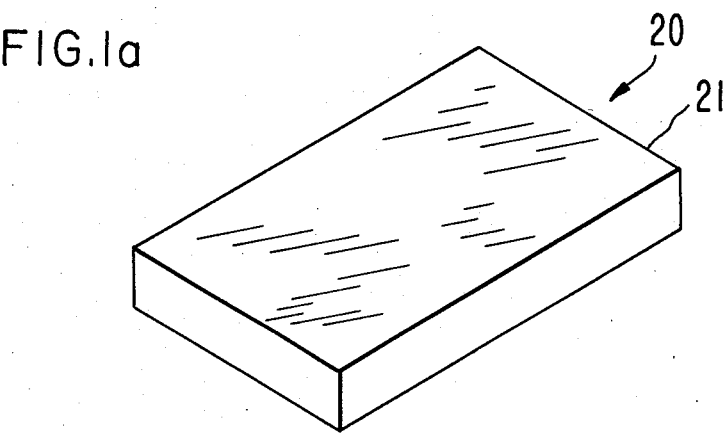
FIGS. 1a and 1b are a general view of a dosage system provided by the invention, which dosage form is designed and shaped for admitting into an environment of use for time-varying patterns of drug delivery including drug-free intervals between drug pulses.
Figure 1B:
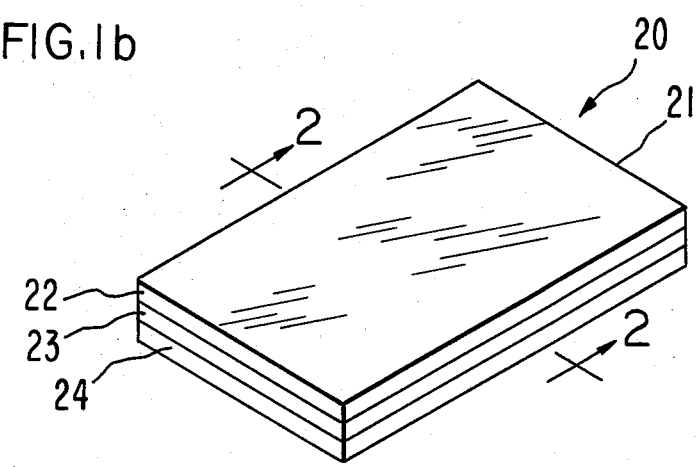

Turning now to the drawing figures in detail, which drawing figures are an example of the dosage form provided by this invention, and which drawing figures are not to be construed as limiting, one example of the programmable agent delivery system is illustrated in FIG. 1a and in FIG. 1b by the numberal 20. In FIGS. 1a and 1b, programmable agent delivery system 20 comprises a body member 21, which body member 21 is seen in FIG. 1b comprising at least three members, a backing member 24, a reservoir 23 and a programmable member 22.

Figure 2:
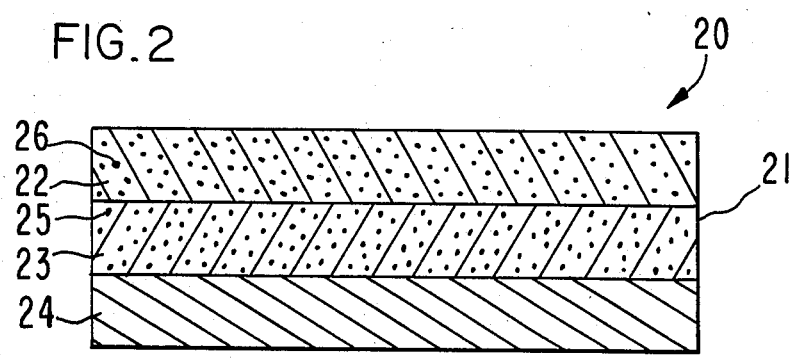
FIG. 2 is an opened view of FIG. 1 for illustrating of the dosage form for providing a time delayed pulse of drug.

Delivery system 20 of FIG. 1b is seen in greater detail in FIG. 2 in cross-section through 2—2 of FIG. 1b. In FIG. 2, delivery system 20 comprises a backing member 24 that is a wall defining one face of delivery system 20, a reservoir 23 that has one surface in contacting relation with backing member 24, and a surface of reservoir 23 in contact with a programmable member 22 that is a wall defining another and different surface of delivery system 20. Backing member 24 is formed of a material that is essentially impermeable to the passage of beneficial agent, mainly a beneficial drug. Typical materials for forming backing member 24 comprise high density polyethylene, metal foil, a laminate comprising a lamina of aluminized polyethylene-terephthalate and a lamina of ethylene-vinyl acetate copolymer, a laminate of a lamina of aluminized polyethyleneterephthalate a lamina of ionomer and a lamina of ethylene-vinyl acetate copolymer, high density polypropylene, nylon, and the like.

Reservoir 23, positioned between backing member 24 and programmable member 22, comprises beneficial agent 25. Reservoir 23 comprises a material permeable to the passage of beneficial agent 25. Representative materials for forming reservoir 23 include polymeric formulations such as polyolefins, polyacrylic acids, polysilicones, copolymers of olefins, esters of olefinic acids, ethylene-vinyl acetate copolymer, ethylene-ethacrylate copolymer, segmented copolymer of butylene terephthalate 33% and polytetramethylene ether terephthalate 67% segmented copolymer of propylene terephthalate 58% and polytetramethylene ether terephthalate, block copolymer of tetramethylene terephthalate-polytetramethylene ether glycol terephthalate, ethylene-vinyl hexanoate copolymer, ethylene-vinyl propionate copolymer, vinyl chloride-diethyl fumarate copolymer, and the like.

The beneficial agent 25 present in reservoir 23 includes any beneficial agent, compound, composition of matter, formulation and the like that can be delivered by agent delivery system 20. In a presently preferred embodiment the beneficial agent 25 includes a drug administered for producing a therapeutic result. The drugs that can be housed and delivered by delivery system 20 include any physiologically or pharmacologically active substance that produces a local or a systemic effect in animals. The term animal includes warm-blooded mammals, humans, primates, household, sport, farm, and zoo animals. The term physiologically as used herein denotes the administration of a drug ot produce normal levels and functions. The term pharmacologically denotes variations in responses to various amounts of drug administered to the host, *Stedman's Medical Dictionary*, 1966, published by Williams and Wilkins Co., Baltimore, MD. The active drugs that can be delivered include inorganic and organic drugs without limitations, drugs that can act on the central nervous system, depressants, hypnotics, sedatives, psychic energizers, tranquilizers, anticonvulsants, muscle relaxants, antiparkinson agents, anti-inflammatories, local anesthetics, muscle contractants, antimicrobials, antimalarials, hormonals, contraceptives, diuretics, sympathomimetrics, antiparasitics, neoplastics, hypoglycemics, ophthalmics, electrolytes, diagnostics, cardiovascular drugs, and the like. The beneficial drugs are known to the art in *Pharmaceutical Sciences*, by Remington, 14 Ed., 1979 published by Mack Publishing Co., Easton, PA, *The Drug, The Nurse, The Patient, Including Current Drug Handbook*, 1974-76 by Falconer et al., published by Sounders Company, Philadelphia, PA; and *Physician's Desk Reference*, 40th Ed., 1986, published by Medical Economics Co., Oradell, N.J.

Programmable member 22 comprises a non-toxic, preferably polymeric formulation comprising an osmotic agent 26. Member 22 is substantially impermeable to the passage of osmotic agent 26 and it is also substantially impermeable to the passage of beneficial agent 25 present in reservoir 23. Member 22 is permeable to the passage of fluid. The osmotic agent 26 present in programmable member 22 is an osmotically active solute, also known as an osmotically active compound, that are soluble in fluid that enter member 22 and they exhibit an osmotic pressure gradient across member 22 against a fluid outside of delivery system 20. Osmotically effective osmagents useful for the present purpose include magnesium sulfate, potassium sulfate, sodium sulfate, lithium sulfate, magnesium chloride, sodium chloride, lithium chloride, magnesium nitrate, potassium nitrate, sodium nitrate, and the like. The salts include also the hydrochlorides, nitrates, hydrobromides, hydroiodides, sulfates, sulfamates and phosphates, and organic acid addition salts such as maleates, acetates, bitartrate, citrate, oxalate, succinate, benzoate, tartrate, fumarate, malate, mandelate, and the like. Osmagent 22 can be in any physical form such as particle, powder, granules, and the like. The amount of active osmagent 26 in member 22 is from about 0.01% to 45%, or higher. The osmotic pressure of active osmagent 26 is measured in a commercially available osmometer that measure vapor pressure differences between pure water and a solution of osmagent, and according to standard thermodynamic principles the vapor pressure ratio is converted into an osmotic pressure difference. The osmometer used for the present measurements is identified as Model 1001-A Vapor Pressure Osmometer, manufactured by Knaurer, W. Germany and distributed by Utopia Instrument Co., Joliet, Ill. The amount of osmagent 26 present in member 22 is about 0.01 to 50 weight percent.

Materials suitable for manufacturing membrane 22 are polymers that are biologically compatible with an animal host, substantially impermeable to the passage of solute 26, permeable to the passage of biological aqueous fluids, and form passageways during operation of delivery system 20. Procedures for ascertaining the impermeability and the permeability of polymeric films are known to the art in Proc. Roy. Sci. London, Series A, Vol. 148, 19835; *J. Pharm. Sci.*, Vol. 55, pp. 1224 to 1229, 1966; *Diffusion In Solids, Liquids and Gases*, by Josh, Chapter XI, pp. 436 to 488, 1980, published by Academic Press Inc., N.Y.

Exemplary materials for fabricating member 22 include a member selected from the group consisting essentially of ethylene vinyl ester copolymers having an ester content of 4 to 80% such as ethylene-vinyl acetate copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl 3-methyl butanoate copolymer, ethylene-vinyl 3-3-dimethyl butanoate copolymer, and ethylene-vinyl benzoate copolymer. Additional exemplary materials suitable for manufacturing member 22 include acrylonitrile-methyl vinyl ether, vinyl chloride-diethyl fumarate, homopolymers and copolymers of partially hydrolyzed poly(vinyl alcohol), plasticized poly(vinyl chloride), plasticized poly(amides), poly(isoprene), poly(isobutylene), lightly cross-linked poly(vinyl pyrrolidone), vinyl-diethyl fumarate copolymers, ethylenepropylene copolymers, polyurethanes, and the like. The polymeric materials are known in *Handbook Of Common Polymers*, by Scott, et al, Sections 1 through 42, published by CRC Press, Cleveland, Ohio.

System 20 in operation dispenses drug 25 over a prolonged period of time. In operation, when system 20 is in a fluid environment, the fluid diffuses into polymeric membrane 22 and dissolves osmagent 26 therein. The rate of fluid imbibition into membrane 22 is related to the osmotic pressure gradient exhibited by the osmagent formulation 26 against an external fluid. As external fluid is imbibed into member 22, it continuously dissolves osmagent 26 forming a solution which solution thereby generates a hydrostatic pressure in membrane 22. This pressure is applied against polymer member 22 causing it to rupture and/or form apertures. Drug 25 then is released through the apertures formed in member 22. Drug 25 is released form system 20 by the inward progressive formation of osmotically-bursting apertures, thereby forming an interior lattice formulation dispensing paths in polymer member 22 for releasing drug 25 through paths in member 22 to the exterior of system 20. The dispensing paths formed in member 22 can be interconnected through tortuous paths of regular and irregular shapes, discernible by microscopic examination. As fluid is imbibed into apertures in contacting relation, it fills the in situ paths and they become a means for enhancing drug 25 transport through reservoir 25 at a controlled rate over a prolonged period of time. The rate and the time of drug 25 released form reservoir 22 is programmed by governing the concentration of osmagent 26 in membrane 22. Thus, if the concentration of osmagent 25 is, for example less than 15 weight percent, system 20 exhibits a longer start-up time accompanied by a smaller quantity of drug released over time; also, if the concentration of osmagent 25 is greater than 15 wt. %, a shorter start-up time is exhibited and a larger quantity of drug 25 is released over time. Procedures for measuring aperture formation resulting in system 10 by the hydrostatic pressure exceeding the cohesive integrity of polymer member 22 with the polymer opening for forming medication releasing paths, can be determined by measurements predicated on pressure-deflection and mechanical behavior measurements techniques reported in *Modern Plastics,* Vol. 41, pp. 143 to 144, 146 and 182, 1964; *Handbook of Common Polymers,* by Scott et al, pp. 588 to 609, 1971; *Machine Design,* 107 to 11, 1975; *J. Sci. Instruments.* Vol. 42, pp. 591 to 596, 1965; and by measuring mechanical stress-strain patterns of polymers using the Instron ® Testing Machine, available from Instron Corporation, Canton, Mass.

Figure 3:
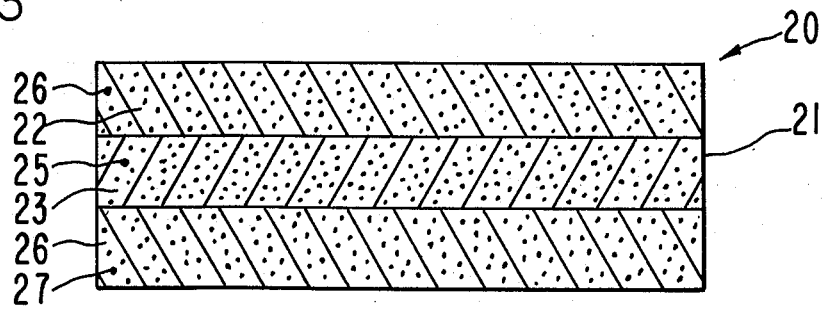
FIG. 3 is an opened view of FIG. 1 for illustrating yet another internal structure or embodiment of the programmable delivery system.

FIG. 3 illustrates, in cross-section, another embodiment of delivery system 20 provided by this invention. In FIG. 3, delivery system 20 comprises reservoir 23 comprising drug formulation 5. Reservoir 23 has one surface in contacting laminar arrangement with a first programable member 22 comprising osmagent 26, with the other and distant surface of reservoir 23 in contacting relation with a second programmable member 27 comprising osmagent 26. System 20 comprises a first and a second programmable member 22 and 27 for providing a greater number of paths for releasing drug 25 from reservoir 23. For example, when system 20 comprises a single programmable member 22, drug 25 is released from a single surface. When system 20 comprises programmable members 22 and 27, drug 25 is released form reservoir 23 through both members to a drug receptor. The use of a pair of drug releasing members 22 and 27 enables reservoir 23 to have a high drug loading of from 0.01 to 50 wt %.

Figure 4:
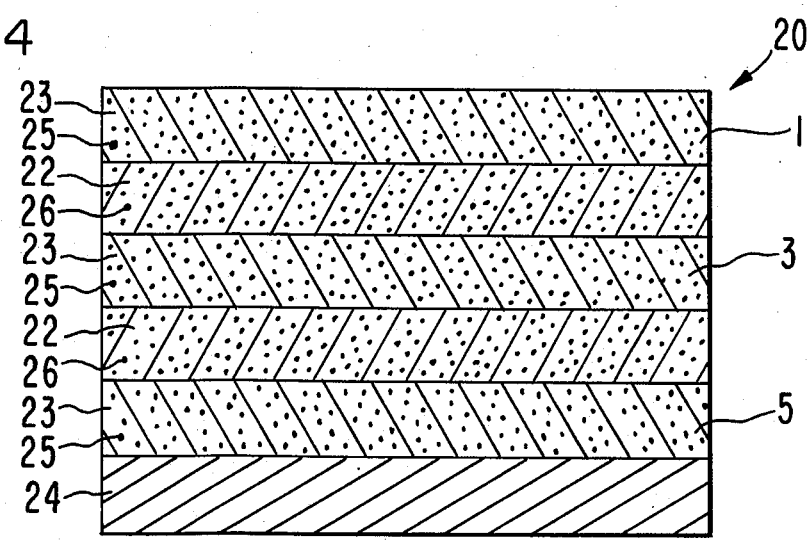
FIG. 4 is an opened view of a programmable dosage form that provides time-varying patterns of drug delivery including drug-free intervals between drug doses of various drug-release durations; and, FIG. 5 is a graph depicting schematic delivery drug delivery time-curves interrupted by drug-free time periods.

FIG. 4 is a cross-section through another delivery system 20 provided by this invention. In FIG. 4, delivery system 20 comprises a multiplicity of reservoirs 23 containing drug 25. The multiplicity of reservoirs 23 are in parallel arrangement and they are separated from each other by a multiplicity of programmable members 22. Programmable members 23 comprise nontoxic, and nontherapeutic osmagent 26. The expression nontherapeutic denotes osmagent 26 is essentially free form therapeutic, physiological and pharmacological activity. Programmable members 22 are in parallel order, they are separated from each other by reservoirs 23, and they are in contact with reservoirs 23. System 20 comprising the multiplicity of consecutive reservoirs 23 interrupted by a multiplicity of consecutive member 22 additionally comprises backing member 24. Backing member 24 is drug-free.

Figure 5:
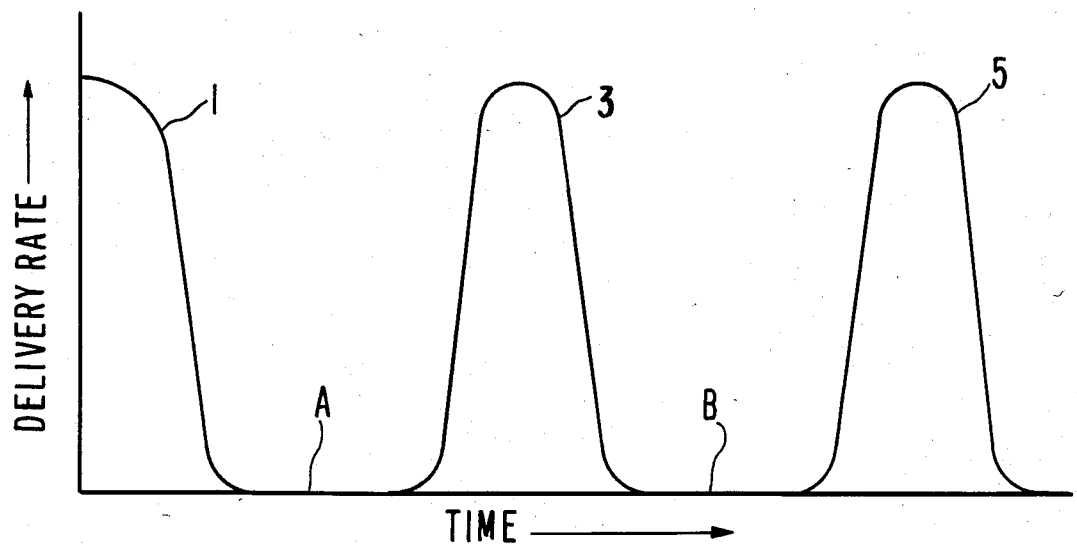

FIG. 5 depicts the release rate profile of delivery system 20 of FIG. 4. In operation, in a biological fluid environment of use, external fluid contacts reservoir 23 which reservoir 23 releases its beneficial drug 25, to produce as seen in FIG. 5, drug release peak 1. Next, system 20 exhibits a period of time during which it does not release any drug as depicted by valley A in FIG. 5. Then, system 20 repeats the pattern of drug delivery as depicted by peaks 3 and 5 that are interrupted by drug-free period B.

The selection of a polymeric member for ascertaining its permeability, or its impermeability to a drug, or to an osmagent can be performed by methods known to the subject art. One technique that can be used is to cast or hot press a film of the polymeric material to a thickness of 1 to 60 mils. The film is used as a barrier between a rapidly stirred, about 150 rpm, saturated solution of the drug and a rapidly stirred solvent bath, both maintained at constant temperature, typically 37° C. Samples are periodically withdrawn from the solvent bath and analyzed for drug concentration. Thus, by plotting the drug concentration in the solvent bath versus time, the permeability or the degree of permeability is determined by Ficke's First Law of diffusion, exemplified by Slope of plot $= Q_1 - Q_2/t_1 - t_2 = PAC/h$, wherein $Q_1$ is the cumulative amount of drug in the solvent in micrograms at $t_1$; $Q_2$ is the cumulative amount of drug in solvent in micrograms at $t_2$; $t_1$ is the elapsed time to the first sample $Q_1$; $t_2$ is the elapsed time to the second sample $Q_2$; A is the area of the film in $cm^2$; C is the initial concentration of drug; and h is the thickness of the film in cm.

While FIGS. 1 through 5 illustrate various delivery system that can be made according to the invention, it is to be understood these, the delivery devices can take a wide variety of shapes, sized and adapted for administering a drug at a controlled rate to different areas of the body. For example, the system includes external and internal delivery systems, such as a tablet, skin patch, ocular insert, sublingual, buccal, implant, vagina, anorectal, delivery systems, and the like.

A delivery system 20 is manufactured by the invention for use as an ocular insert as follows: first 75 g of ethylene-vinyl acetate copolymer having a vinyl acetate content of 38% on a Barbender Plasticorder ® bowl equipped with roller blades, which copolymer is masticated for 2 to 4 minutes, is added 20 grams of pilocarpine nitrate and the polymer and the drug blended for 20 minutes at 40 rpm. Next, the contents of the bowl are removed and fed to the hopper of an extruder, and extruded as a film. Then, the procedure is repeated by feeding sodium chloride and ethylene-vinyl acetate copolymer having as vinyl acetate content of 28% to the bowl, which is masticated, fed to the extruder and extruded into a film. The first prepared fell then is pressed laminated to one surface of the second prepared film. Next, a film of high density polyethylene is laminated to the other surface of the first prepared film, to yield system 20 of FIG. 2. The system is then punched into 13.5×5.8 mm ocular inserts for administering pilocarpine nitrate to the eye.

In summary, it will be readily appreciated that the present invention contributes to the art an unobvious drug delivery device possessing wide and practical application. While the invention has been described and pointed out in detail and with reference to operative embodiments thereof, it will be understood that those skilled in the art will appreciate that various changes, modifications, substitutions and omissions can be made without departing form the spirit of the invention. It is intended, therefore, that the invention embrace those equivalents within the scope of the claims which follow.

I claim:

1. A delivery system for delivering a beneficial drug at a controlled rate to a biological environment, wherein the delivery system is comprised of: (a) a reservoir comprising a first surface and a second surface, which reservoir is dimensioned for use and retention in a biological environment, the reservoir comprising a polymeric formulation that is pervious to the passage of drug; (b) a beneficial drug in the reservoir; (c) a first wall occluding the first surface of the reservoir, the first wall essentially-free of drug and impervious to the passage of drug; (d) a second wall occluding the second surface of the reservoir, the second wall comprising a polymeric formulation substantially impervious to the passage of an osmotically effective solute; and (e) an osmotically effective solute in the second wall.

* * * * *